United States Patent
Wildner et al.

(10) Patent No.: US 6,790,447 B1
(45) Date of Patent: Sep. 14, 2004

(54) PEPTIDES FOR TREATMENT OF AUTOIMMUNE DISEASES

(76) Inventors: Gerhild Wildner, Rupprechtstrasse 8a, 80636 München (DE); Stephan Thurau, Sendlinger Strasse 28, 80331 München (DE)

(*) Notice: Subject to any disclaimer, the term of this patent is extended or adjusted under 35 U.S.C. 154(b) by 0 days.

(21) Appl. No.: 08/727,529

(22) PCT Filed: Apr. 21, 1995

(86) PCT No.: PCT/EP95/01512

§ 371 (c)(1),
(2), (4) Date: Oct. 18, 1996

(87) PCT Pub. No.: WO95/29194

PCT Pub. Date: Nov. 2, 1995

(30) Foreign Application Priority Data

Apr. 21, 1994 (DE) .......................................... 44 13 938

(51) Int. Cl.⁷ .............................................. A61K 39/00
(52) U.S. Cl. ........................ 424/185.1; 514/12; 514/13; 514/14; 514/15
(58) Field of Search ...................... 424/185.1; 514/12.15

(56) References Cited

FOREIGN PATENT DOCUMENTS

| WO | WO 94/04171 | 3/1994 |
|---|---|---|
| WO | WO 94/04557 | 3/1994 |

OTHER PUBLICATIONS

The Merck Manual of Diagnosis and Therapy, 17th Ed, pp. 725–728, 1999.*
Goldsby et al. Immunology. 5$^{th}$ Ed., pp. 170–172, 2003.*
Thurau, S., et al., J. Autiommun. 4:504–516(1991).
Wildner G. and Thuran, S.R., Eur. J. Immunol. 24:2579–2585 (1994).

* cited by examiner

*Primary Examiner*—Patrick J. Nolan
(74) *Attorney, Agent, or Firm*—Thaddius J. Carvis (57) ABSTRACT

The invention refers to peptides consisting of 7 to 20 amino acid residues with the sequence A-Leu-B-Ser-C-Thr-Ala-Ala-D, in which B and C are each an amino acid or amino acids and A and D are each monomeric or polymeric organic groups, and especially those, in which B is serine, threonine or leucine and/or in which C is threonine, tryptophane, glutamic acid or serine. The monomeric or polymeric organic groups can independently of each other consist especially of one or several amino acid residues, organic aliphatic groups, especially fatty acids or lipopolysaccharides. The peptides according to the invention are preferentially used for the preparation of a therapeutic composition for the treatment of autoimmune diseases, especially for the treatment of uveitis. In this context the peptides are especially useful for the preparation of a therapeutic composition for the immunization against retinal S-antigen or interphotoreceptor retinol binding protein. Tolerance can be induced orally.

3 Claims, 2 Drawing Sheets

SEQUENCE LISTING (1) GENERAL INFORMATION:

(iii) NUMBER OF SEQUENCES: 47

(2) INFORMATION FOR SEQ ID NO: 1

(i) SEQUENCE CHARACTERISTICS:
      (A) LENGTH: 7 residues
      (B) TYPE: amino acid
      (C) STRANDEDNESS: single
      (D) TOPOLOGY: linear    (ii) MOLECULE TYPE: <Unknown>
      (A) DESCRIPTION: peptide    (xi) SEQUENCE DESCRIPTION: SEQ ID NO: 1:

Leu Xaa Ser Xaa Thr Ala Ala
           5

(2) INFORMATION FOR SEQ ID NO: 2

(i) SEQUENCE CHARACTERISTICS:
      (A) LENGTH: 9 residues
      (B) TYPE: amino acid
      (C) STRANDEDNESS: single
      (D) TOPOLOGY: linear    (ii) MOLECULE TYPE: <Unknown>
      (A) DESCRIPTION: peptide    (xi) SEQUENCE DESCRIPTION: SEQ ID NO: 2:

Leu Xaa Ser Xaa Thr Ala Ala Asp Glu
           5

(2) INFORMATION FOR SEQ ID NO: 3

(i) SEQUENCE CHARACTERISTICS:
      (A) LENGTH: 16 residues (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 3:

Xaa Ala Leu Asn Glu Asp Leu Ser Ser Trp Thr Ala Ala Asp Thr
            5                   10                  15

Xaa (2) INFORMATION FOR SEQ ID NO: 4

(i) SEQUENCE CHARACTERISTICS:
        (A) LENGTH: 14 residues
        (B) TYPE: amino acid
        (C) STRANDEDNESS: single
        (D) TOPOLOGY: linear (ii) MOLECULE TYPE: <Unknown>
        (A) DESCRIPTION: B27PD peptide (xi) SEQUENCE DESCRIPTION: SEQ ID NO: 4:

Ala Leu Asn Glu Asp Leu Ser Ser Trp Thr Ala Ala Asp Thr
            5                   10

(2) INFORMATION FOR SEQ ID NO: 5

(i) SEQUENCE CHARACTERISTICS:
        (A) LENGTH: 14 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 5:

Phe Leu Gly Glu Leu Thr Ser Ser Glu Val Ala Thr Glu Val
            5                   10

(2) INFORMATION FOR SEQ ID NO: 6

(i) SEQUENCE CHARACTERISTICS:
        (A) LENGTH: 14 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 6:

Ala Leu Asn Glu Asp Leu Arg Ser Trp Thr Ala Ala Asp Thr
            5                   10

(2) INFORMATION FOR SEQ ID NO: 7

(i) SEQUENCE CHARACTERISTICS:
        (A) LENGTH: 21 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: <Unknown>

```
Leu Arg Ser Trp Thr Ala Ala Asp Thr Ala Ala Gln Ile Thr Gln
                 5                  10                  15
Arg Lys Trp Glu Ala Ala
             20
```

(2) INFORMATION FOR SEQ ID NO: 8

(i) SEQUENCE CHARACTERISTICS:
        (A) LENGTH: 17 residues
        (B) TYPE: amino acid
        (C) STRANDEDNESS: single
        (D) TOPOLOGY: linear     (ii) MOLECULE TYPE: <Unknown>
        (A) DESCRIPTION: peptide     (xi) SEQUENCE DESCRIPTION: SEQ ID NO: <Unknown>

```
Asp Leu Arg Ser Trp Thr Ala Ala Asp Thr Ala Ala Gln Ile Thr
                 5                  10                  15
Gln Arg
```

(2) INFORMATION FOR SEQ ID NO: 9

(i) SEQUENCE CHARACTERISTICS:
        (A) LENGTH: 16 residues
        (B) TYPE: amino acid
        (C) STRANDEDNESS: single
        (D) TOPOLOGY: linear     (ii) MOLECULE TYPE: <Unknown>
        (A) DESCRIPTION: peptide     (xi) SEQUENCE DESCRIPTION: SEQ ID NO: <Unknown>

```
Asp Leu Arg Ser Trp Thr Ala Ala Asp Thr Ala Ala Gln Ile Thr
                 5                  10                  15
Gln
```

(2) INFORMATION FOR SEQ ID NO: 10

(i) SEQUENCE CHARACTERISTICS:
        (A) LENGTH: 14 residues
        (B) TYPE: amino acid
        (C) STRANDEDNESS: single
        (D) TOPOLOGY: linear     (ii) MOLECULE TYPE: <Unknown>
        (A) DESCRIPTION: peptide     (xi) SEQUENCE DESCRIPTION: SEQ ID NO: <Unknown>

```
Asp Leu Ser Trp Thr Ala Ala Asp Thr Ala Ala Gln Ile Thr
                 5                  10
```

(2) INFORMATION FOR SEQ ID NO: 11

(i) SEQUENCE CHARACTERISTICS:
        (A) LENGTH: 17 residues
        (B) TYPE: amino acid
        (C) STRANDEDNESS: single
        (D) TOPOLOGY: linear     (ii) MOLECULE TYPE: <Unknown>
        (A) DESCRIPTION: peptide     (xi) SEQUENCE DESCRIPTION: SEQ ID NO: <Unknown>

```
Asp Leu Ser Ser Trp Thr Ala Ala Asp Thr Ala Ala Gln Ile Thr
                 5                  10                  15
Gln Arg
```

```
(2) INFORMATION FOR SEQ ID NO: 12

(i) SEQUENCE CHARACTERISTICS:
        (A) LENGTH: 20 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: <Unknown>

Asp Leu Ser Ser Trp Thr Ala Ala Asp Thr Ala Ala Gln Ile Thr
                 5                  10                  15

Gln Arg Lys Trp Glu
                20

(2) INFORMATION FOR SEQ ID NO: 13

(i) SEQUENCE CHARACTERISTICS:
        (A) LENGTH: 19 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: <Unknown>

Asp Leu Arg Ser Trp Thr Ala Ala Asp Thr Ala Ala Gln Ile Thr
                 5                  10                  15

Gln Arg Lys Trp (2) INFORMATION FOR SEQ ID NO: 14

(i) SEQUENCE CHARACTERISTICS:
        (A) LENGTH: 18 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: <Unknown>

Leu Arg Ser Trp Thr Ala Ala Asp Thr Ala Ala Gln Ile Thr Gln
                 5                  10                  15

Arg Lys Trp (2) INFORMATION FOR SEQ ID NO: 15

(i) SEQUENCE CHARACTERISTICS:
        (A) LENGTH: 22 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: <Unknown>

Asp Leu Ser Ser Trp Thr Ala Ala Asp Thr Ala Ala Gln Ile Thr
                 5                  10                  15

Gln Arg Lys Trp Glu Ala Ala
                20
```

(2) INFORMATION FOR SEQ ID NO: 16

(i) SEQUENCE CHARACTERISTICS:
        (A) LENGTH: 18 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: <Unknown>

Asp Leu Ser Ser Trp Thr Ala Ala Asp Thr Ala Ala Gln Ile Thr
                  5                  10                  15

Gln Arg Lys (2) INFORMATION FOR SEQ ID NO: 17

(i) SEQUENCE CHARACTERISTICS:
        (A) LENGTH: 8 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 17:

Leu Xaa Ser Xaa Xaa Thr Ala Ala
                  5

(2) INFORMATION FOR SEQ ID NO: 18

(i) SEQUENCE CHARACTERISTICS:
        (A) LENGTH: 9 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 18:

Leu Xaa Xaa Ser Xaa Xaa Thr Ala Ala
                  5

(2) INFORMATION FOR SEQ ID NO: 19

(i) SEQUENCE CHARACTERISTICS:
        (A) LENGTH: 8 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 19:

Leu Xaa Xaa Ser Xaa Thr Ala Ala
                  5

(2) INFORMATION FOR SEQ ID NO: 20

(i) SEQUENCE CHARACTERISTICS:
        (A) LENGTH: 9 residues
        (B) TYPE: amino acid
        (C) STRANDEDNESS: single
        (D) TOPOLOGY: linear

```
       (ii) MOLECULE TYPE: <Unknown>
            (A) DESCRIPTION: peptide (xi) SEQUENCE DESCRIPTION: SEQ ID NO: 20:

Leu Xaa Ser Xaa Xaa Xaa Thr Ala Ala
                  5

(2) INFORMATION FOR SEQ ID NO: 21

(i) SEQUENCE CHARACTERISTICS:
            (A) LENGTH: 10 residues
            (B) TYPE: amino acid
            (C) STRANDEDNESS: single
            (D) TOPOLOGY: linear (ii) MOLECULE TYPE: <Unknown>
            (A) DESCRIPTION: peptide (xi) SEQUENCE DESCRIPTION: SEQ ID NO: 21:

Leu Xaa Xaa Ser Xaa Xaa Xaa Thr Ala Ala
                  5                  10

(2) INFORMATION FOR SEQ ID NO: 22

(i) SEQUENCE CHARACTERISTICS:
            (A) LENGTH: 9 residues
            (B) TYPE: amino acid
            (C) STRANDEDNESS: single
            (D) TOPOLOGY: linear (ii) MOLECULE TYPE: <Unknown>
            (A) DESCRIPTION: peptide (xi) SEQUENCE DESCRIPTION: SEQ ID NO: 22:

Leu Xaa Xaa Xaa Ser Xaa Thr Ala Ala
                  5

(2) INFORMATION FOR SEQ ID NO: 23

(i) SEQUENCE CHARACTERISTICS:
            (A) LENGTH: 10 residues
            (B) TYPE: amino acid
            (C) STRANDEDNESS: single
            (D) TOPOLOGY: linear (ii) MOLECULE TYPE: <Unknown>
            (A) DESCRIPTION: peptide (xi) SEQUENCE DESCRIPTION: SEQ ID NO: 23:

Leu Xaa Xaa Xaa Ser Xaa Xaa Thr Ala Ala
                  5                  10

(2) INFORMATION FOR SEQ ID NO: 24

(i) SEQUENCE CHARACTERISTICS:
            (A) LENGTH: 10 residues
            (B) TYPE: amino acid
            (C) STRANDEDNESS: single
            (D) TOPOLOGY: linear (ii) MOLECULE TYPE: <Unknown>
            (A) DESCRIPTION: peptide (xi) SEQUENCE DESCRIPTION: SEQ ID NO: 24:

Leu Xaa Xaa Ser Xaa Thr Ala Ala Asp Glu
                  5                  10

(2) INFORMATION FOR SEQ ID NO: 25
```

-continued

```
    (i) SEQUENCE CHARACTERISTICS:
        (A) LENGTH: 10 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 25:

Leu Xaa Ser Xaa Xaa Thr Ala Ala Asp Glu
                 5                  10

(2) INFORMATION FOR SEQ ID NO: 26

(i) SEQUENCE CHARACTERISTICS:
        (A) LENGTH: 11 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 26:

Leu Xaa Xaa Ser Xaa Xaa Thr Ala Ala Asp Glu
                 5                  10

(2) INFORMATION FOR SEQ ID NO: 27

(i) SEQUENCE CHARACTERISTICS:
        (A) LENGTH: 11 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 27:

Leu Xaa Ser Xaa Xaa Xaa Thr Ala Ala Asp Glu
                 5                  10

(2) INFORMATION FOR SEQ ID NO: 28

(i) SEQUENCE CHARACTERISTICS:
        (A) LENGTH: 11 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 28:

Leu Xaa Xaa Xaa Ser Xaa Thr Ala Ala Asp Glu
                 5                  10

(2) INFORMATION FOR SEQ ID NO: 29

(i) SEQUENCE CHARACTERISTICS:
        (A) LENGTH: 12 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 29:
```

```
Leu Xaa Xaa Ser Xaa Xaa Xaa Thr Ala Ala Asp Glu
              5                  10
```

(2) INFORMATION FOR SEQ ID NO: 30

(i) SEQUENCE CHARACTERISTICS:
        (A) LENGTH: 12 residues
        (B) TYPE: amino acid
        (C) STRANDEDNESS: single
        (D) TOPOLOGY: linear     (ii) MOLECULE TYPE: <Unknown>
        (A) DESCRIPTION: peptide     (xi) SEQUENCE DESCRIPTION: SEQ ID NO: 30:

```
Leu Xaa Xaa Xaa Ser Xaa Xaa Thr Ala Ala Asp Glu
              5                  10
```

(2) INFORMATION FOR SEQ ID NO: 31

(i) SEQUENCE CHARACTERISTICS:
        (A) LENGTH: 30 residues
        (B) TYPE: amino acid
        (C) STRANDEDNESS: single
        (D) TOPOLOGY: linear     (ii) MOLECULE TYPE: <Unknown>
        (A) DESCRIPTION: peptide     (xi) SEQUENCE DESCRIPTION: SEQ ID NO: 31:

```
Ala Leu Asn Glu Asp Leu Ser Ser Trp Thr Ala Ala Asp Thr Xaa
              5                  10                      15

Xaa Xaa Xaa Xaa Xaa Xaa Xaa Xaa Xaa Xaa Xaa Xaa Xaa Xaa Xaa
              20                  25                      30
```

(2) INFORMATION FOR SEQ ID NO: 32

(i) SEQUENCE CHARACTERISTICS:
        (A) LENGTH: 30 residues
        (B) TYPE: amino acid
        (C) STRANDEDNESS: single
        (D) TOPOLOGY: linear     (ii) MOLECULE TYPE: <Unknown>
        (A) DESCRIPTION: peptide     (xi) SEQUENCE DESCRIPTION: SEQ ID NO: 32:

```
Xaa Ala Leu Asn Glu Asp Leu Ser Ser Trp Thr Ala Ala Asp Thr
              5                  10                      15

Xaa Xaa Xaa Xaa Xaa Xaa Xaa Xaa Xaa Xaa Xaa Xaa Xaa Xaa Xaa
              20                  25                      30
```

(2) INFORMATION FOR SEQ ID NO: 33

(i) SEQUENCE CHARACTERISTICS:
        (A) LENGTH: 30 residues
        (B) TYPE: amino acid
        (C) STRANDEDNESS: single
        (D) TOPOLOGY: linear     (ii) MOLECULE TYPE: <Unknown>
        (A) DESCRIPTION: peptide     (xi) SEQUENCE DESCRIPTION: SEQ ID NO: 33:

```
Xaa Xaa Ala Leu Asn Glu Asp Leu Ser Ser Trp Thr Ala Ala Asp
              5                  10                      15

Thr Xaa Xaa Xaa Xaa Xaa Xaa Xaa Xaa Xaa Xaa Xaa Xaa Xaa Xaa
              20                  25                      30
```

(2) INFORMATION FOR SEQ ID NO: 34

(i) SEQUENCE CHARACTERISTICS:
        (A) LENGTH: 30 residues
        (B) TYPE: amino acid
        (C) STRANDEDNESS: single
        (D) TOPOLOGY: linear     (ii) MOLECULE TYPE: <Unknown>
        (A) DESCRIPTION: peptide     (xi) SEQUENCE DESCRIPTION: SEQ ID NO: 34:

```
Xaa Xaa Xaa Ala Leu Asn Glu Asp Leu Ser Ser Trp Thr Ala Ala
                 5                  10                  15
Asp Thr Xaa Xaa Xaa Xaa Xaa Xaa Xaa Xaa Xaa Xaa Xaa Xaa Xaa
                20                  25                  30
```

(2) INFORMATION FOR SEQ ID NO: 35

(i) SEQUENCE CHARACTERISTICS:
        (A) LENGTH: 30 residues
        (B) TYPE: amino acid
        (C) STRANDEDNESS: single
        (D) TOPOLOGY: linear     (ii) MOLECULE TYPE: <Unknown>
        (A) DESCRIPTION: peptide     (xi) SEQUENCE DESCRIPTION: SEQ ID NO: 35:

```
Xaa Xaa Xaa Xaa Ala Leu Asn Glu Asp Leu Ser Ser Trp Thr Ala
                 5                  10                  15
Ala Asp Thr Xaa Xaa Xaa Xaa Xaa Xaa Xaa Xaa Xaa Xaa Xaa Xaa
                20                  25                  30
```

(2) INFORMATION FOR SEQ ID NO: 36

(i) SEQUENCE CHARACTERISTICS:
        (A) LENGTH: 30 residues
        (B) TYPE: amino acid
        (C) STRANDEDNESS: single
        (D) TOPOLOGY: linear     (ii) MOLECULE TYPE: <Unknown>
        (A) DESCRIPTION: peptide     (xi) SEQUENCE DESCRIPTION: SEQ ID NO: 36:

```
Xaa Xaa Xaa Xaa Xaa Ala Leu Asn Glu Asp Leu Ser Ser Trp Thr
                 5                  10                  15
Ala Ala Asp Thr Xaa Xaa Xaa Xaa Xaa Xaa Xaa Xaa Xaa Xaa Xaa
                20                  25                  30
```

(2) INFORMATION FOR SEQ ID NO: 37

(i) SEQUENCE CHARACTERISTICS:
        (A) LENGTH: 30 residues
        (B) TYPE: amino acid
        (C) STRANDEDNESS: single
        (D) TOPOLOGY: linear     (ii) MOLECULE TYPE: <Unknown>
        (A) DESCRIPTION: peptide     (xi) SEQUENCE DESCRIPTION: SEQ ID NO: 37:

```
Xaa Xaa Xaa Xaa Xaa Xaa Ala Leu Asn Glu Asp Leu Ser Ser Trp
                 5                  10                  15
Thr Ala Ala Asp Thr Xaa Xaa Xaa Xaa Xaa Xaa Xaa Xaa Xaa Xaa
```

20 25 30

(2) INFORMATION FOR SEQ ID NO: 38

(i) SEQUENCE CHARACTERISTICS:
       (A) LENGTH: 30 residues
       (B) TYPE: amino acid
       (C) STRANDEDNESS: single
       (D) TOPOLOGY: linear     (ii) MOLECULE TYPE: <Unknown>
       (A) DESCRIPTION: peptide     (xi) SEQUENCE DESCRIPTION: SEQ ID NO: 38:

Xaa Xaa Xaa Xaa Xaa Xaa Xaa Ala Leu Asn Glu Asp Leu Ser Ser
              5              10            15

Trp Thr Ala Ala Asp Thr Xaa Xaa Xaa Xaa Xaa Xaa Xaa Xaa Xaa
            20            25            30

(2) INFORMATION FOR SEQ ID NO: 39

(i) SEQUENCE CHARACTERISTICS:
       (A) LENGTH: 30 residues
       (B) TYPE: amino acid
       (C) STRANDEDNESS: single
       (D) TOPOLOGY: linear     (ii) MOLECULE TYPE: <Unknown>
       (A) DESCRIPTION: peptide     (xi) SEQUENCE DESCRIPTION: SEQ ID NO: 39:

Xaa Xaa Xaa Xaa Xaa Xaa Xaa Xaa Ala Leu Asn Glu Asp Leu Ser
              5              10            15

Ser Trp Thr Ala Ala Asp Thr Xaa Xaa Xaa Xaa Xaa Xaa Xaa Xaa
            20            25            30

(2) INFORMATION FOR SEQ ID NO: 40

(i) SEQUENCE CHARACTERISTICS:
       (A) LENGTH: 30 residues
       (B) TYPE: amino acid
       (C) STRANDEDNESS: single
       (D) TOPOLOGY: linear     (ii) MOLECULE TYPE: <Unknown>
       (A) DESCRIPTION: peptide     (xi) SEQUENCE DESCRIPTION: SEQ ID NO: 40:

Xaa Xaa Xaa Xaa Xaa Xaa Xaa Xaa Xaa Ala Leu Asn Glu Asp Leu
              5              10            15

Ser Ser Trp Thr Ala Ala Asp Thr Xaa Xaa Xaa Xaa Xaa Xaa Xaa
            20            25            30

(2) INFORMATION FOR SEQ ID NO: 41

(i) SEQUENCE CHARACTERISTICS:
       (A) LENGTH: 30 residues
       (B) TYPE: amino acid
       (C) STRANDEDNESS: single
       (D) TOPOLOGY: linear     (ii) MOLECULE TYPE: <Unknown>
       (A) DESCRIPTION: peptide     (xi) SEQUENCE DESCRIPTION: SEQ ID NO: 41:

Xaa Xaa Xaa Xaa Xaa Xaa Xaa Xaa Xaa Xaa Ala Leu Asn Glu Asp
              5              10            15

```
Leu Ser Ser Trp Thr Ala Ala Asp Thr Xaa Xaa Xaa Xaa Xaa
            20                  25                  30
```

(2) INFORMATION FOR SEQ ID NO: 42

(i) SEQUENCE CHARACTERISTICS:
        (A) LENGTH: 30 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 42:

```
Xaa Xaa Xaa Xaa Xaa Xaa Xaa Xaa Xaa Xaa Xaa Ala Leu Asn Glu
                5                   10                  15
Asp Leu Ser Ser Trp Thr Ala Ala Asp Thr Xaa Xaa Xaa Xaa Xaa
            20                  25                  30
```

(2) INFORMATION FOR SEQ ID NO: 43

(i) SEQUENCE CHARACTERISTICS:
        (A) LENGTH: 30 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 43:

```
Xaa Xaa Xaa Xaa Xaa Xaa Xaa Xaa Xaa Xaa Xaa Xaa Ala Leu Asn
                5                   10                  15
Glu Asp Leu Ser Ser Trp Thr Ala Ala Asp Thr Xaa Xaa Xaa Xaa
            20                  25                  30
```

(2) INFORMATION FOR SEQ ID NO: 44

(i) SEQUENCE CHARACTERISTICS:
        (A) LENGTH: 30 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 44:

```
Xaa Xaa Xaa Xaa Xaa Xaa Xaa Xaa Xaa Xaa Xaa Xaa Xaa Ala Leu
                5                   10                  15
Asn Glu Asp Leu Ser Ser Trp Thr Ala Ala Asp Thr Xaa Xaa Xaa
            20                  25                  30
```

(2) INFORMATION FOR SEQ ID NO: 45

(i) SEQUENCE CHARACTERISTICS:
        (A) LENGTH: 30 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 45:

```
Xaa Xaa Xaa Xaa Xaa Xaa Xaa Xaa Xaa Xaa Xaa Xaa Xaa Xaa Ala
                5                   10                  15
```

```
Leu Asn Glu Asp Leu Ser Ser Trp Thr Ala Ala Asp Thr Xaa Xaa
                20                  25                  30

(2) INFORMATION FOR SEQ ID NO: 46

(i) SEQUENCE CHARACTERISTICS:
        (A) LENGTH: 30 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 46:

Xaa Xaa Xaa Xaa Xaa Xaa Xaa Xaa Xaa Xaa Xaa Xaa Xaa Xaa Xaa
                 5                  10                  15

Ala Leu Asn Glu Asp Leu Ser Ser Trp Thr Ala Ala Asp Thr Xaa
                20                  25                  30

(2) INFORMATION FOR SEQ ID NO: 47

(i) SEQUENCE CHARACTERISTICS:
        (A) LENGTH: 30 residues
        (B) TYPE: amino acid
        (C) STRANDEDNESS: single
        (D) TOPOLOGY: linear (ii) MOLECULE TYPE: <Unknown>
        (A) DESCRIPTION: peptide (xi) SEQUENCE DESCRIPTION: SEQ ID NO: 47:

Xaa Xaa Xaa Xaa Xaa Xaa Xaa Xaa Xaa Xaa Xaa Xaa Xaa Xaa Xaa
                 5                  10                  15

Xaa Ala Leu Asn Glu Asp Leu Ser Ser Trp Thr Ala Ala Asp Thr
                20                  25                  30
```

PEPTIDES FOR TREATMENT OF AUTOIMMUNE DISEASES

RELATED APPLICATION DATA

This is a continuation-in-part of international application PCT/EP95/01512, filed Apr. 21, 1995, claiming benefit of German Pat. Ap. No. P44 13 938.1, filed Apr. 21, 1994.

BACKGROUND OF THE INVENTION

Autoimmune diseases (rheumatoid arthritis, multiple sclerosis, ulcerative colitis, autoimmune uveitis and many others) are diseases in which the immune system does not tolerize self structures of the body, but attacks them like an intruding pathogen. Consequently, body tissue is damaged or even destroyed and pain and physical defects occur (e.g., stiff joints in rheumatoid arthritis; general motion inhibition, incontinence, and speech disability in multiple sclerosis; severe diarrhea, nutritional defects and gut perforation with fatal outcome in ulcerative colitis; in uveitis impaired visual acuity, which can even lead to blindness).

Uveitis is an intraocular inflammation which affects iris, ciliary body vitreous, retina and/or the choroid. With the iris involved inflammation is often painful and can lead to loss of pupillary reaction through iris synechia at its front with the cornea and/or with the lens at its back. Cellular precipitates on the inner side of the cornea and the lens as well as cellular infiltrates in the anterior chamber and the vitreous of the eye, sometimes followed by the development of hazy membranes, which stretch through the vitreous or lay on the retina like a curtain, impair visual acuity. Signs of inflammation of retina and choroid are edema, cellular infiltrates and, in later stages, atrophic changes. Not rarely are the retinal vessels involved in the inflammation. Edematous swellings of the optic nerve papilla can additionally lead to the disturbance of the neuronal processing of light perception. While the described phenomena are partially reversible, destruction of the retinal architecture is an irreversible event, which leads to a lasting impairment of visual acuity and even to blindness.

The described uveitis symptoms can be associated with other autoimmune diseases, e.g., rheumatic diseases or post infectious. The inflammation is initiated by the immune system and other cells are involved in its further course.

In most cases autoimmune diseases are chronic, either relapsing or permanently progressive. In rare cases the tissues, which have been destroyed by the immune system, can be regenerated. If nerve tissue is involved, like in multiple sclerosis or uveitis, a regeneration is not possible. The causes of these autoimmune diseases are mostly unknown, in some cases infections are suspected, which misguide the immune system.

Conventional therapies, that are initiated in cases of immune diseases, target not only the self reactive ("autoaggressive") part of the immune system, but generally suppress immunoreactive cells, which should serve in the defense of invaded pathogens or tumor cells. Besides an impaired general immune defense and the probable development of tumors, conventional therapies with immuno suppressive agents like steroids, cyclosporin A and cytotoxic agents have also many non-immunologic and sometimes life threatening side effects.

In many autoimmune diseases an inherited predisposition is suspected on the grounds of statistical correlations of the disease with certain histocompatibility antigens (HLA, originally described as transplantation antigens). As a mechanism, it is postulated that the immune system confuses pathogen antigens (bacteria, virus) with self HLA-antigens.

Over the last years many attempts have been undertaken to interfere with the regulation of the immune system in order to reinstitute the normal balance of self tolerance and pathogen defense. Amongst others, attempts have been made to induce an immunologic tolerance via "immunologically privileged" sites of the organism. One example of a privileged site is the mammalian gut, which can be used to induce tolerance ("oral tolerance") to protein molecules ("antigens"). This mechanism supposedly prevents, that an immune reaction against digested food is continuously generated. The oral administration of "autoantigens" (self proteins, against which the aggressive immune response is directed in the case of autoimmune diseases), can therefore induce tolerance, i.e., non-responsiveness to self tissue, even if the site of autoaggression, which is the affected tissue, is spatially far distant from the gut. Oral tolerance induction is a form of immunosuppression, which is highly specific, i.e., the immune reaction affects only the implied antigen. Therefore side effects comparable to those in general immunosuppression are not to be expected. Undesired pharmacological-toxicological effects have not yet been observed in oral applications of autoantigens and are not expected.

The autoantigens are known in some autoimmune diseases and can therefore be used for specific therapies. In some cases there is only one antigen against which the immune reaction is directed (collagen II in rheumatoid arthritis, insulin in diabetes), in the case of autoimmune uveitis two proteins from the photoreceptor layer of the eye are known, which can induce uveitis in the animal model and against which an immune response can be detected in uvietis patients.

These are the retinal S-antigen and the interphotoreceptor-retinoid-binding protein (IRBP). Within these proteins are certain sections (epitopes), which also can induce uveitis if applied as peptides. An experimental uveitis induced by these means can be prevented, if S-antigen, IRBP or peptides thereof are applied orally (oral tolerance). (See, e.g., Thurau, S. R., Chan, C.-C., Suh, E., Nussenblatt, R. B.: Induction of oral tolerance to S-antigen induced experimental autoimmune uveitis by a uveitogenic 20 mer peptide. *J. Autoimm.* 4: 507–516 (1991). This and the other paper and patent cited herein arm hereby incorporated in their entireties by reference.)

The provision of protein antigens is associated with major difficulties. Moreover, there are a number of disadvantages:
1) Generally the antigen must be isolated from natural tissues. During the process infections (viruses, viroids, bacteria) or transfections with (retro)viral or bacterial DNA probably occur.
2) The antigen can at best with great expense be synthesized genetically.
3) In individual cases, long-term storage of proteins like protein antigens can be difficult. In unfavorable cases, even costly storing conditions can guarantee stability, activity and effectiveness of a protein only for a short time period.

4) The risk of developing an allergy like food allergy or contact allergy is increased with protein antigens, because of a crosslinking on cell surfaces. This is especially important in patients with autoimmune diseases, since there is an increased number of patients with allergies.

The invention will address and solve these problems.

SUMMARY OF THE INVENTION

The problem will be addressed and solved by a peptide as described in the claims.

The invention refers on the one hand to a peptide consisting of 7 to 30 amino acid residues with the sequence A-Leu-B-Ser-C-Thr-Ala-Ala-D (SEQ ID NOS. 1 and 18 to 24), wherein B and C are each an amino acid or amino acids and A and D are each monomeric or polymeric organic groups.

In addition it has been established that a peptide, which is extended carboxyterminally by the two amino acids, aspartic acid and glutaric acid, compared to the aforementioned core sequence -Leu-B-Ser-C-Thr-Ala-Ala- (residues 2 to 8 of SEQ ID NO: 1), has also outstanding therapeutic features.

Accordingly an additional claim of the invention is a peptide consisting of 9 to 30 amino acids with the sequence A-Leu-B-Ser-C-Thr-Ala-Ala-Asp-Glu-D (SEQ ID NOS. 2 and 25 to 31), wherein again B and C are each in amino acid or amino acids and A and D are each monomeric or polymeric organic groups.

DETAILED DESCRIPTION OF THE INVENTION

In the course of the investigation leading to the invention it could be demonstrated that the binding of peptides according to the invention to the T-cell-receptor and HLA (human leukocyte antigen) is distributed discontinuously over several amino acids within the core sequence. In between these for the binding essential amino acids are residues which do not participate in the binding and can therefore be exchanged. A continuous sequence of amino acids seems not to be crucial for the function, but single positions within the peptide, which simultaneously interacts with the T cell receptor and the HLA-antigen.

Accordingly before and behind the core sequence with 7 or 9 amino acids, respectively (position A or position D) as well as within the core sequence (position B and C) amino acids can be exchanged without a major loss of biological function.

The variable positions B and C lie within the 7 or 9 residues long core sequence and stand for one or several amino acids. Variations herein are only possible within relative narrow limits, because stearic conditions within the core sequence play a pivotal role for the biological relevant interaction of single positions of the core sequence with the HLA-molecule and the T cell receptor. Our investigations have shown, that B and C preferably stand for a single amino acid, respectively.

Particularly the invention refers to peptides according to the aforementioned features, in which B stands for serine or threonine. In experiments it has been demonstrated repeatedly, that the amino acids in position B of the core sequence can be exchanged. In the course of the investigations it was also shown that a substitution of group B by arginine does not yield therapeutically active peptides.

In a preferred form of the peptide according to the invention C refers to threonine, tryptophane, glutamic acid or serine. But also in this case other amino acids can be introduced in this position of the core sequence without significantly altering the therapeutic effectiveness. Therefore the amino acid in position C of the peptides according to the invention seems to be of less importance for the binding within the HLA-peptide-T cell-receptor-complex.

When the peptides according to the invention integrate into the HLA-peptide-T cell-receptor-complex, with respect to the core sequence, amino- and carboxyterminally located groups A and D seem to be positioned outside of the binding site and therefore play an only minor biological-functional role. Therefore a great number of groups of different length and different bulkiness can be located in these positions without significantly altering the therapeutic effectiveness of the peptides.

The monomeric or polymeric organic groups A and D, for instance, comprise independently of each other one or several amino acids, organic aliphatic groups, especially saturated or unsaturated fatty acid residues or also lipopolysaccharides.

If A and D are amino acid groups, then the number of amino- and carboxyterminal residues for the sequence of claim 1 is calculated according to the following rules:

0 to 23 amino acid residues in the aminoterminal group A, and 0 or up to maximal (23-number of amino acids in aminoterminal group A) amino acid residues in the arboxyterminal group D.

In the case of a peptic, whose core sequence is carboxyterminally extended by two amino acids according to claim 9, the number of amino- and carboxyterminal residues is calculated according to the following rules:

0 to 21 amino acid residues in the aminoterminal group A, and 0 or up to maximal (21-number of amino acids in aminoterminal group A) amino acid residues in the carboxyterminal group D.

The term peptide according to the invention also refers to those amino acids chains, which exhibit N-terminal and C-terminal substitutions. Examples for substitutions are:

acetylation, formation of esters with fatty acids, conjugation with sugars, alkylation with $C_1$- to $C_{12}$-alkyl-or alkenyl groups.

The peptide according to the invention and the above definition comprises preferably 7 or 9 to 20, especially 8 or 9 to 16 amino acid residues.

The peptide preferably comprises the following sequence:

A$_m$-Ala-Leu-Asn-Glu-Asp-Leu-Ser-Ser-Trp-Thr-Ala-Ala-Asp-Thr-D$_n$ (SEQ ID NO: 3 and SEQ ID NOS. 32 to 48, or truncated versions thereof having fewer Xaa groups.

wherein A and D are one or several amino acids and m and n show the number of amino acid residues according to the following rule:

m=0 to 16 and n=0 or up to maximal (16-m).

For the treatment of autoimmune diseases comprising administration of an above-described peptide, administration of the following peptides are excluded:

Leu-Arg-Ser-Trp-Thr-Ala-Ala-Asp-Thr-Ala-Ala-Gln-Ile-Thr-Gln-Arg-Lys-Trp-Glu-Ala-Ala (SEQ ID NO: 7);

Asp-Leu-Arg-Ser-Trp-Thr-Ala-Ala-Asp-Thr-Ala-Ala-Gln-Ile-Thr-Gln-Arg (SEQ ID NO: 8);

Asp-Leu-Arg-Ser-Trp-Thr-Ala-Ala-Asp-Thr-Ala-Ala-Gln-Ile-Thr-Gln (SEQ ID NO: 9);

Asp-Leu-Ser-Trp-Thr-Ala-Ala-Asp-Thr-Ala-Ala-Gln-Ile-Thr (SEQ ID NO: 10);

Asp-Leu-Ser-Ser-Trp-Thr-Ala-Ala-Asp-Thr-Ala-Ala-Gln-Ile-Thr-Gln-Arg (SEQ ID NO: 11);

Asp-Leu-Ser-Ser-Trp-Thr-Ala-Ala-Asp-Thr-Ala-Ala-Gln-Ile-Thr-Gln-Arg-Lys-Trp-Glu (SEQ ID NO: 12);

Asp-Leu-Arg-Ser-Trp-Thr-Ala-Ala-Asp-Thr-Ala-Ala-Gln-Ile-Thr-Gln-Arg-Lys-Trp (SEQ ID NO: 13);

Leu-Arg-Ser-Trp-Thr-Ala-Ala-Asp-Thr-Ala-Ala-Gln-Ile-Thr-Gln-Arg-Lys-Trp (SEQ ID NO: 14);

Asp-Leu-Ser-Ser-Trp-Thr-Ala-Ala-Asp-Thr-Ala-Ala-Gln-Ile-Thr-Gln-Arg-Lys-Trp-Glu-Ala-Ala (SEQ ID NO: 15);

Asp-Leu-Ser-Ser-Trp-Thr-Ala-Ala-Asp-Thr-Ala-Ala-Gln-Ile-Thr-Gln-Arg-Lys (SEQ ID No. 16) (see WO 94/04171 to Urban, et at., 1994).

A peptide could be identified, which does not originate from a retinal protein, but which is far more effective with respect to its therapeutic potency than the previously described derivative of the of the retinal S-antigen. This 14 mer peptide of the invention with the sequence Ala-Leu-Asn-Glu-Asp-Leu-Ser-Ser-Trp-Thr-Ala-Ala-Asp-Thr (SEQ ID NO: 4)

is most effective in suppression of uveitis if administered orally. This peptide has up to now not in any respect been functionally associated with uveitis, not with respect to induction of the disease, nor its therapy.

Another special feature of this peptide consists of its ability to suppress the S-antigen specific immune response as well as the reactivity to the protein chemically unrelated IRBP when given orally.

Subject-matter of this invention also includes use of a peptide of the invention for the preparation of a therapeutic composition for the treatment of autoimmune diseases and specifically for the treatment of uveitis.

An additional subject of this invention is also the use of a peptide according to the invention for the preparation of a remedy for immunization against the retinal S-antigen, against the interphotoreceptor retinol binding (IRBP) and/or against human leukocyte antigens, which contain the sequence Ala-Leu-Asn-Glu-Asp-Leu-Ser-Ser-Trp-Thr-Ala-Ala-Asp-Thr (SEQ ID NO: 4)

The above-mentioned therapeutic compositions produced according to the invention can be applied as solution, suspension or compressed. In these cases customary additives and carriers are added to the active ingredient.

Following the administration of the therapeutic preparation tolerance can be induced via the oral route. A daily dosage of about 10 µg to about 10 mg of peptide per kilogram body weight should be administered.

The effect of the peptides according to the invention can be a regulatory effect on the immune system on the basis of a cross reactivity with other self antigens. Therefore the applicability of the peptides of the invention for the therapy of multiple autoimmune diseases can be expected.

The reactivity of the immune system in this context is not restricted to blood lymphocytes. The humoral immune response (antibodies), macrophages and other cells of the immune system can also be potential targets of the peptides according to the invention.

The therapeutic potential has been demonstrated in animal experiments. Groups of 8–16 Lewis rats (age 6–8 weeks, weight ca. 200 grams) have been fed with the peptide B27PD, the corresponding retinal protein (retinal S-antigen (S-Ag) or IRBP), a peptide of the retinal S-antigen (truncated equivalent to P35: PDSAg), an irrelevant control protein (ovalbumin from hen egg (OVA)), an irrelevant control peptide (B7PD) or physiological salt solution (PBS).

The amino acid sequences of the above mentioned peptides B27PD, PDSAg and B7PD have been as follows, with the amino acid designation given in the one-letter-code (A=Ala, C=Cys, D=Asp, E=Glu, F=Phe, G=Gly, H=His, I=Ile, K=Lys, L=Leu, M=Met, N=Asn, P=Pro, Q=Gln, R=Arg, S=Ser, T=Thr, V=Val, W=Trp, and Y=Tyr; the full amino acid sequences using the U.S. Patent Office format are set forth hereinafter in the Sequence Listing section of this application):

B27PD: A-L-N-E-D-L-S-S-W-T-A-A-D-T (SEQ ID NO: 4)

PDSAg: F-L-G-E-L-T-S-S-E-V-A-T-E-V (SEQ ID NO: 5)

B7PD: A-L-N-E-D-L-R-S-W-T-A-A-D-T (SEQ ID NO: 6)

Of these peptides B27PD and PDSAg are uveitogenic, i.e., after immunization of objects with the peptides they develop uveitis. In contrast B7PD does not have any uveitogenic properties.

The peptides have been applied orally every other day at dosages of 200 µg each time dissolved in PBS, while the proteins were used in 1 mg dosages. Two days after the third and final administration of the proteins or peptides, respectively, uveitis was induced by immunization with the retinal antigens (S-antigen or IRBP, 35 or 20 µg, respectively, emulsified in adjuvant), which are well known to induce uveitis in the rat model.

In control animals, which were not orally tolerized, disease occurred 10 to 14 days after immunization. Due to animal protection laws, the experiments were terminated three to four days after the last animals in the positive control groups diseased.

The protective effect of orally administered antigens was clinically seen by an ameliorated course of the disease or completely missing clinical symptoms, which was confirmed by histological examination. The histological evaluation consists of a grading of inflammatory signs in the tissue and destruction of the retina, the clinical grading refers to inflammatory signs of the conjunctiva and the anterior segment of the eye, which can be observed readily and are not necessarily correlated with the visual acuity.

Figure 1:
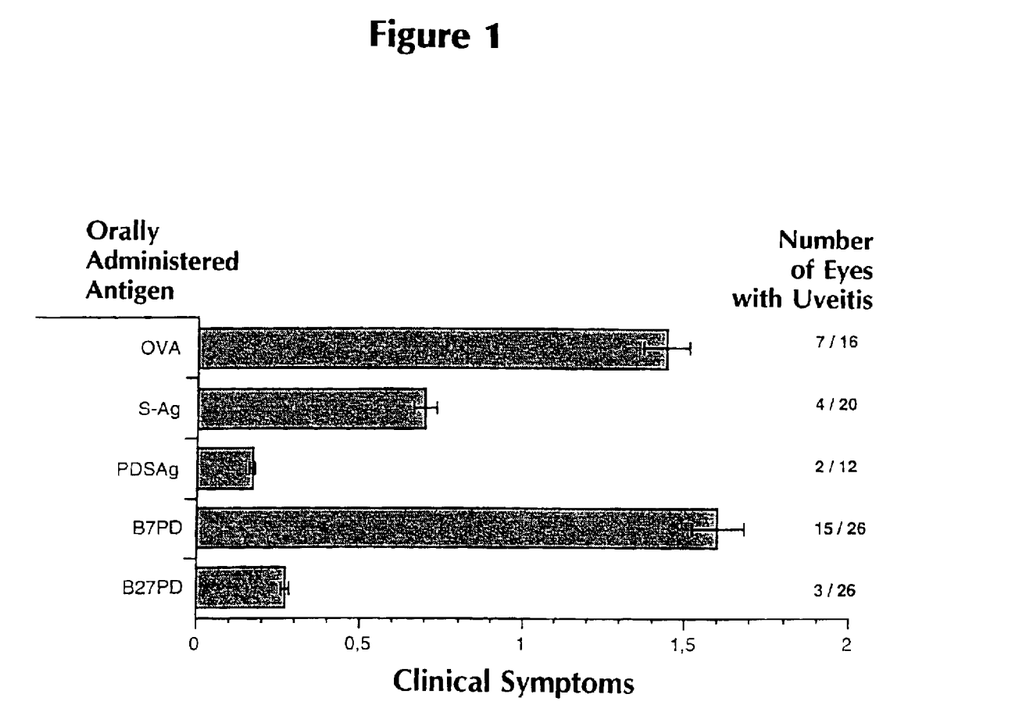
FIG. 1 shows the severity of a S-antigen-induced uveitis after oral administration of different antigens (oral tolerance).

The results, which have been obtained in the above described experiments in the animal model, are depicted in the following figures:

FIG. 1, which shows the severity of a S-antigen-induced uveitis after oral administration of different antigens (oral tolerance), demonstrates that in the case of induction with S-antigen the clinical symptoms can be reduced to 16% through the oral administration of B27PD (PDSAg: 9%, S-ag: 41%) compared to the group, which has been fed with control protein (ovalbumin).

An additional histological evaluation revealed that uveitis in the B27PD fed animal group was, compared to ovalbumin fed control groups, reduced by 57%, after S-antigen feeding uveitis was also reduced by 57% and after feeding with S-antigen-peptide uveitis was reduced by only 14%.

Figure 2:
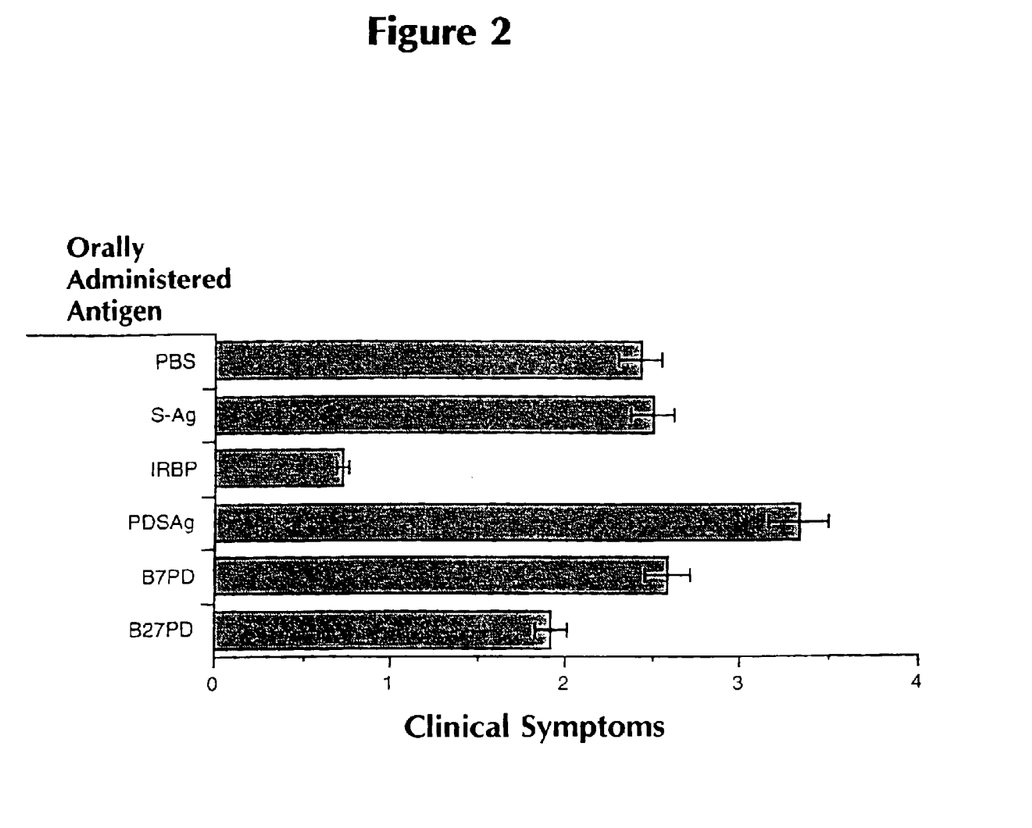
FIG. 2 indicates the severity of an IRBP induced uveitis after oral administration of different antigens (oral tolerance).

FIG. 2 indicates the severity of an IRBP induced uveitis after oral administration of different antigens (oral tolerance). The figure shows that in the case of induction with IRBP PBS, S-antigen and also PDSAg, which is active against S-antigen, have no therapeutic properties. The clinical symptoms, however, can be reduced to 75% by B27PD-feeding, compared to the maximal disease obtained in the PBS-fed group. After feeding IRBP itself, the clinical score for uveitis is reduced to 25%.

It was demonstrated that different changes can be made in peptide B27PD without major loss of effectiveness. Some of these changes include:

1) The peptide can be elongated at the N-terminal as well as the C-terminal end.
2) The peptide can be truncated at the N-terminal as well as the C-terminal end by some (up to 6) amino acid residues.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method to induce tolerance in a patient having an autoimmune disease or predisposed to an autoimmune disease said disease being uveitis comprising orally administering to the patient an effective amount of a peptide comprising 14 to 30 amino acid residues which comprise the sequence:

Ala-Leu-Asn-Glu-Asp-Leu-Ser-Ser-Trp-Thr-Ala-Ala-Asp-Thr (SEQ ID NO: 4)

wherein the sequence may be truncated at the N-terminal as well as the C-terminal end by up to 2 amino acid residues, wherein said peptide administered comprises at least 14 amino acids, and wherein the core sequence of Leu-Ser-Ser-Trp-Thr-Ala-Ala (SEQ ID NO: 1)

may show variations selected from the group consisting of:
Leu-Ser-Ser-Thr-Thr-Ala-Ala (SEQ ID NO: 1)
Leu-Ser-Ser-Glu-Thr-Ala-Ala (SEQ ID NO: 1)
Leu-Thr-Ser-Thr-Thr-Ala-Ala (SEQ ID NO: 1) and
Leu-Thr-Ser-Glu-Thr-Ala-Ala (SEQ ID NO: 1).

2. A method according to claim 1 wherein the peptide is Ala-Leu-Asn-Glu-Asp-Leu-Ser-Ser-Trp-Thr-Ala-Ala-Asp-Thr (SEQ ID NO: 4).

3. A method according to claim 1 wherein the peptide bears an N-terminal or C-terminal organic group selected from the group consisting of an acetyl group, a fatty acid ester, a sugar, or a $C_1$–$C_{12}$ alkyl or alkenyl group.

* * * * *